(12) United States Patent
Mikkaichi

(10) Patent No.: US 10,932,763 B2
(45) Date of Patent: Mar. 2, 2021

(54) TISSUE COLLECTING TOOL AND TISSUE COLLECTING SYSTEM

(71) Applicant: OLYMPUS CORPORATION, Hachioji (JP)

(72) Inventor: Takayasu Mikkaichi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 419 days.

(21) Appl. No.: 15/877,961

(22) Filed: Jan. 23, 2018

(65) Prior Publication Data

US 2018/0146958 A1 May 31, 2018

Related U.S. Application Data

(63) Continuation of application No. PCT/JP2015/071213, filed on Jul. 27, 2015.

(51) Int. Cl.
*A61B 10/04* (2006.01)
*A61B 1/00* (2006.01)
*A61B 10/02* (2006.01)
*A61B 10/06* (2006.01)
*A61B 17/00* (2006.01)
(Continued)

(52) U.S. Cl.
CPC ............... *A61B 10/04* (2013.01); *A61B 1/00* (2013.01); *A61B 1/005* (2013.01); *A61B 1/00087* (2013.01); *A61B 10/0096* (2013.01); *A61B 10/02* (2013.01); *A61B 10/06* (2013.01); *A61B 17/00234* (2013.01); *A61B 2017/00278* (2013.01); *A61B 2017/00287* (2013.01)

(58) Field of Classification Search
None
See application file for complete search history.

(56) References Cited

U.S. PATENT DOCUMENTS 4,750,475 A * 6/1988 Yoshihashi ............ A61B 10/04
600/131
5,190,555 A 3/1993 Wetter et al.
2004/0255739 A1 12/2004 Clifford et al.
(Continued)

FOREIGN PATENT DOCUMENTS

DE 4204210 A1 8/1992
JP H05-088095 A 4/1993
(Continued)

OTHER PUBLICATIONS

March 22, 2019 extend European Search Report issued in European Patent Application No. 15899587.8.
(Continued)

*Primary Examiner* — Etsub D Berhanu
*Assistant Examiner* — Aurelie H Tu
(74) *Attorney, Agent, or Firm* — Oliff PLC

(57) ABSTRACT

A tissue collecting tool includes: a main body that is long; an operation part arranged on a proximal end side of the main body; a bag part including a bottom portion and an opening portion and having a part of the opening portion fixed to the main body such that the opening portion is positioned on a further proximal end side than the bottom portion; and a linear member connected to the opening portion and the operation part and raising the opening portion by being moved in a longitudinal direction of the main body.

12 Claims, 9 Drawing Sheets

(51) Int. Cl.
*A61B 1/005* (2006.01)
*A61B 10/00* (2006.01)

(56) References Cited

U.S. PATENT DOCUMENTS

| | | |
|---|---|---|
| 2010/0152612 A1 | 6/2010 | Headley, Jr. et al. |
| 2010/0152746 A1 | 6/2010 | Ceniccola et al. |
| 2014/0371760 A1 | 12/2014 | Menn |

FOREIGN PATENT DOCUMENTS

| | | |
|---|---|---|
| JP | 2002-345824 A | 12/2002 |
| JP | 2007-082675 A | 4/2007 |
| JP | 2007-523676 A | 8/2007 |
| JP | 2010-099477 A | 5/2010 |
| JP | 2012-143538 A | 8/2012 |
| JP | 5087429 B2 | 12/2012 |
| JP | 2013-027616 A | 2/2013 |
| JP | 2015-000340 A | 1/2015 |

OTHER PUBLICATIONS

Oct. 20, 2015 Search Report issued in International Patent Application No. PCT/JP2015/071213.

\* cited by examiner

TISSUE COLLECTING TOOL AND TISSUE COLLECTING SYSTEM

This application is a continuation application based on a PCT Patent Application No. PCT/JP2015/071213, filed on Jul. 27, 2015. The content of the PCT Application is incorporated herein by reference.

TECHNICAL FIELD

The present invention relates to a tissue collecting tool and a tissue collecting system that collects tissues from the inside of a body through a trans-natural opening.

BACKGROUND ART

Conventionally, a treatment of collecting a body tissue is performed using a treatment tool inserted into a channel of a flexible endoscope. In a case in which a tissue to be collected is a pathologic tissue such as a tumor or the like, the resected tissue is grasped using grasping forceps or the like and removed together with an endoscope or received in a collecting tool attached to an endoscope. As collecting tools, for example, collecting tools disclosed in Japanese Unexamined Patent Application, First Publication No. 2007-82675 and Japanese Unexamined Patent Application, First Publication No. H5-88095 are known.

SUMMARY OF INVENTION

According to a first aspect of the present invention, the tissue collecting tool includes; a main body which has a long shape; an operation part which is provided in a proximal end side of the main body; a bag part which includes a bottom portion and an opening portion and in which a part of the opening portion is fixed to the main body such that the opening portion is positioned closer to a proximal end of the bag part than the bottom portion; and a linear member which is connected to the opening portion and the operation part and which is configured to raise the opening portion by being moved in a longitudinal direction of the main body.

According to a second aspect of the present invention, in the tissue collecting tool of the first aspect, the tissue collecting tool may further include a wire part which is capable of being elastically transformed. The wire part may be provided along the opening portion. In the bag part, the linear member and the wire part may be connected to the opening portion at a position separate from a fixing portion where the opening portion is fixed to the main body. The wire part may be configured so as to be capable of raising from the fixing portion as a starting point by a movement of the linear member with respect to the main body in a direction of a longitudinal axis of the main body.

According to a third aspect of the present invention, in the tissue collecting tool of the first or second aspect, the main body may be a tube-shaped member. The linear member may be inserted into a lumen of the main body from an opening formed at a position arranged closer to the proximal end of the main body than the fixing portion, and a proximal end portion of the linear member may be connected to the operation part.

According to a fourth aspect of the present invention, in the tissue collecting tool of the third aspect, the wire part may include: a wire bending portion that is inserted into the lumen of the main body and is exposed outside the main body through a through hole formed on a side face of the main body, and is arranged in the opening portion; and a proximal end portion that is connected to the operation part at the proximal end portion of the main body. An opening width of the opening portion is configured to be adjustable by a movement of the wire part with respect to the main body in the direction of the longitudinal axis.

According to a fifth aspect of the present invention, a tissue collecting system includes: an endoscope which has a flexible insertion part; the tissue collecting tool according to any one of claims 1 to 4 that is arranged in a direction of a longitudinal axis of the insertion part on an outer edge of the insertion part; and a grasping tool which is inserted into a channel formed in the insertion part.

According to a sixth aspect of the present invention, in the tissue collecting system of the fifth aspect, the bag part may be configured to be capable of being opened such that the opening portion is raised so as to face a distal end of the insertion part by moving the linear member in the direction of the longitudinal axis with respect to the main body in a state in which the bag part is pushed further toward a distal end side than a distal end of the insertion part of the endoscope.

According to a seventh aspect of the present invention, in the tissue collecting system of the fifth aspect, tissue collecting tool may be fixed on an outer edge of the insertion part closer to a proximal end side of the insertion part than the bending portion of the insertion part.

DESCRIPTION OF EMBODIMENTS

Figure 1:
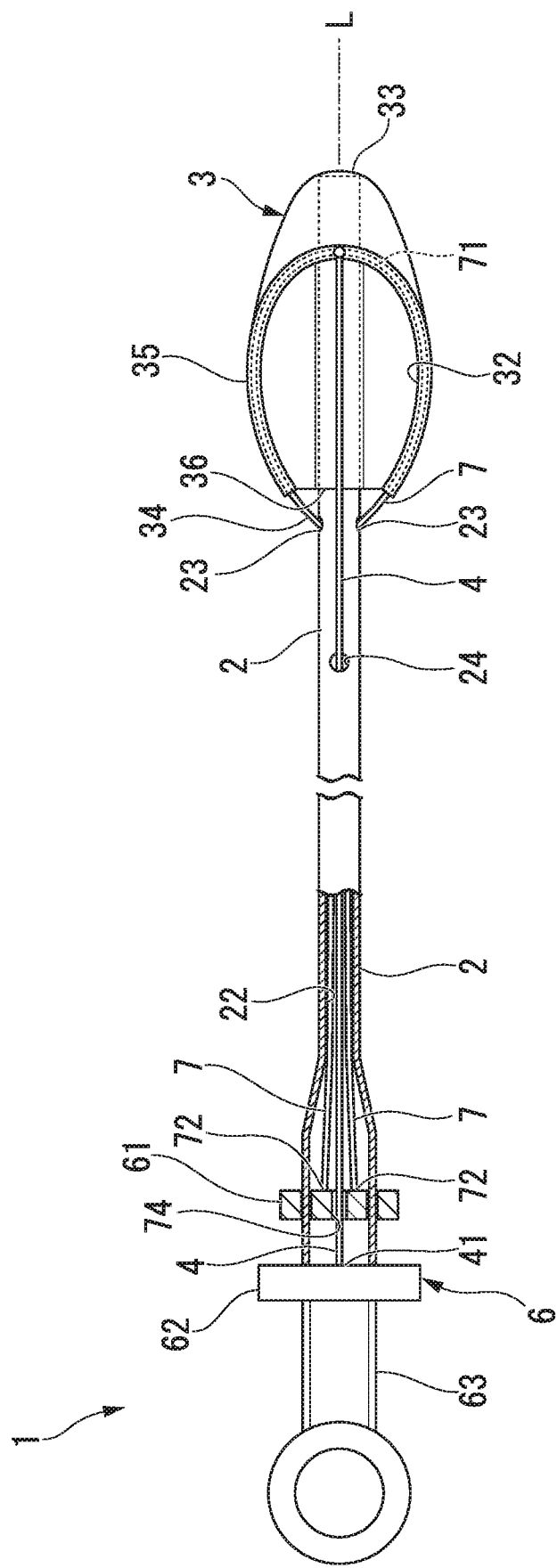
FIG. 1 is a side view of a tissue collecting tool according to one embodiment of the present invention.

A tissue collecting tool and a tissue collecting system according to one embodiment of the present invention will be described with reference to FIGS. 1 to 9. FIG. 1 is a side view of a tissue collecting tool 1 (hereinafter, simply referred to as a "collecting tool") according to one embodiment of the present invention and is a diagram showing a part of an operation part in a cross-section taken in a direction of a longitudinal axis L. Hereinafter, in an endoscope and the collecting tool 1 to be described later, an insertion part side with respect to an operation part of the endoscope will be referred to as a distal end side, and an operation part side of the endoscope with respect to an insertion part will be referred to as a proximal end side.

As shown in FIG. 1, the collecting tool 1 includes an inner sheath (main body) 2 having a long shape, a bag part 3, a string (linear member) 4, an operation part 6, and a first wire (wire part) 7.

The inner sheath 2 includes a lumen 22 extending from a distal end 21 to a proximal end. The bag part 3 is arranged in the distal end portion of the inner sheath 2. The operation part 6 is arranged in the proximal end portion of the inner sheath 2.

Figure 3:
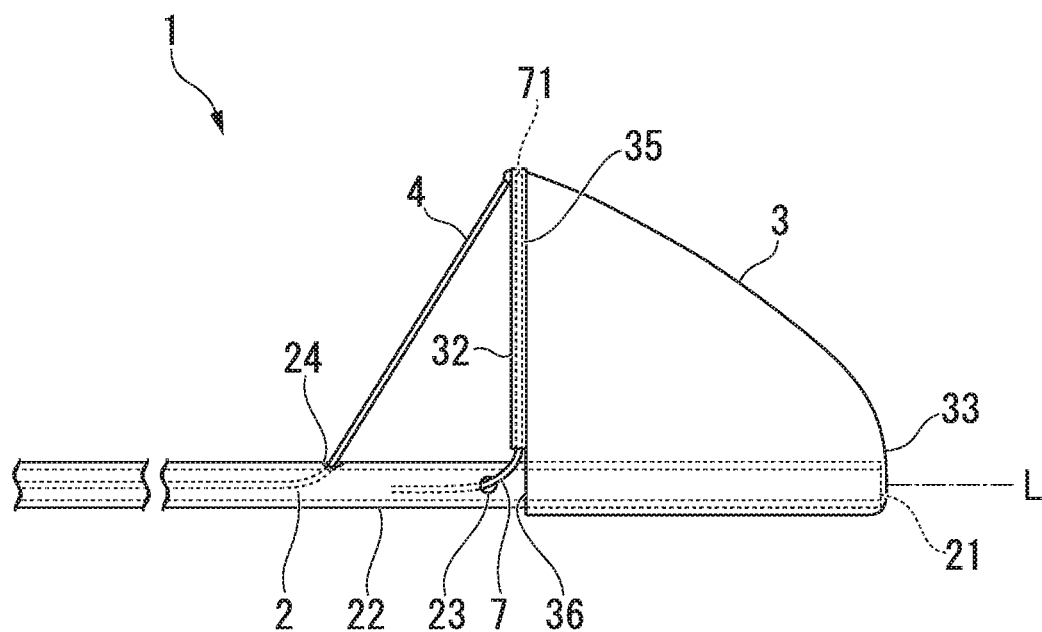
FIG. 3 is a side view showing a distal end portion of a tissue collecting tool according to one embodiment of the present invention.

The bag part 3 includes an opening portion 32 and a bottom portion 33. As shown in FIG. 3, in the bag part 3, the bottom portion 33 is positioned at the distal end 21 of the inner sheath 2, and the opening portion 32 is positioned closer to the proximal end side than the bottom portion 33. The distal end portion of the inner sheath 2 is inserted into the bag part 3, and the distal end portion of the inner sheath 2 is fixed to the bag part 3 using a locking hole (not shown in the drawing) arranged in the bag part 3, an adhesive agent, or the like.

The bag part 3, for example, is a bag formed using a material such as vinyl or the like and formed as a thin film that can separate a resected tissue or liquid.

The first wire 7 can be elastically transformed and includes a wire bending portion 71 of which a center portion in the longitudinal direction is folded, a portion between the wire bending portion 71 and the proximal end portion 72 is inserted into and passes through the lumen 22 of the inner sheath 2, and both proximal end portions 72 are connected to a first slider 61 of the operation part 6. Accordingly, the first wire 7 is connected to the bag part 3 in the wire bending portion 71, both proximal end portions 72 are connected to the operation part 6, and the first wire 7 is inserted into and passes through the inside of the lumen 22 to be capable of advancing or retreating with respect to the inner sheath 2.

The first wire 7 is formed using a shape memory alloy such as nickel titanium or the like that can be elastically transformed, and a bent shape is given to the wire bending portion 71 arranged in the bag part 3 in advance. When an external force is applied, the first wire 7 is elastically transformed and has a restoring force toward the bent shape in a natural state.

In the opening portion 32, the first wire 7 is arranged along a peripheral end edge of the opening portion 32. In the opening portion 32, an insertion passage 35 through which the first wire 7 is capable of being inserted is formed along the opening portion 32, and the wire bending portion 71 is inserted inside the insertion passage 35. The first wire 7 exposed from the insertion passage 35 is inserted into one pair of first holes 23 formed to face each other on the side face of the inner sheath 2.

The opening portion 32 is connected to the string 4 at a position separate from a fixing portion 36 fixed with the inner sheath 2. In the inner sheath 2, a second hole (opening) 24 is formed closer to the proximal end side than the fixing portion 36 fixed with the opening portion 32. The proximal end side of the string 4 is inserted into the inner sheath 2 through the second hole 24, extends up to the operation part 6, and is connected to a second slider 62 of the operation part 6. The string 4 moves to the proximal end side in the direction of the longitudinal axis L with respect to the inner sheath 2, thereby the string 4 pulls a bending portion of the first wire 7, changes the direction of the opening portion 32, and raises the opening portion 32.

The operation part 6 is arranged on the proximal end side of the inner sheath 2. The operation part 6 includes an operation part main body 63, a first slider 61, and a second slider 62. In the first slider 61, the proximal end portion 72 of the first wire 7 is fixed, and the first slider 61 is arranged to be slidable with respect to the operation part main body 63. In the second slider 62, the proximal end portion 41 of the string 4 is fixed, and the second slider 62 is arranged to be slidable with respect to the operation part main body 63. The second slider 62 is positioned closer to the proximal end side than the first slider 61. In the first slider 61, a through hole 74 extending in the direction of the longitudinal axis L is formed, and the string 4 is inserted into the through hole 74.

Figure 2:
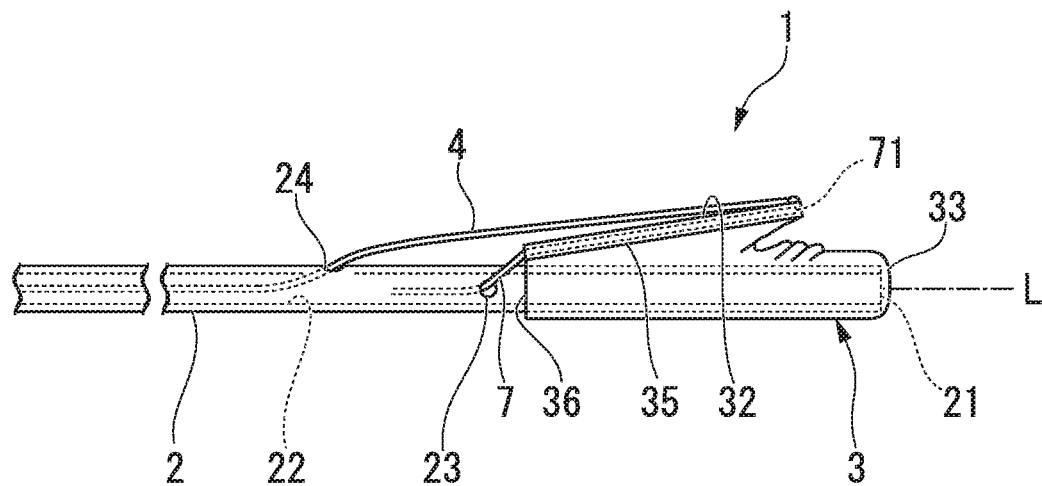
FIG. 2 is a side view showing a distal end portion of a tissue collecting tool according to one embodiment of the present invention.

Next, the operation of the collecting tool 1 will be described. FIG. 2 is a side view showing the collecting tool 1 seen in a direction orthogonal to the longitudinal axis L of the inner sheath 2 and shows a state before the opening portion 32 is raised. FIG. 3 is a side view of the collecting tool 1 seen in a direction orthogonal to the longitudinal axis L of the inner sheath 2 and shows a state in which the opening portion 32 is raised. In the description presented below, as shown in FIG. 2, a state in which the opening portion 32 is along the inner sheath 2 and the bag part 3 is contracted will be referred to as a closed state. In addition, as shown in FIG. 3, a state in which the opening portion 32 is raised and is open in the proximal end direction of the inner sheath 2 will be referred to as an open state.

The length of the string 4 is set such that the bag part 3 is in the closed state in a case in which the second slider 62 is positioned on the distal end side with respect to the operation part main body 63. When the second slider 62 slides to the proximal end side with respect to the operation part main body 63, the string 4 is pulled to the proximal end side inside the lumen 22 of the inner sheath 2 to generate tension, and a connection portion between the string 4 and the opening portion 32 is pulled to the proximal end side. At this time, the bending portion of the first wire 7 arranged in the opening portion 32 is pulled to the proximal end side and is raised, and the open state shown in FIG. 3 is formed. In the open state, the opening portion 32 is open toward the proximal end side, and the bag part 3 is in the open state.

When the first slider 61 moves to the proximal end side with respect to the operation part main body 63, both proximal end portions 72 of the first wire 7 are moved to the proximal end side with respect to the inner sheath 2. The first wire 7 is inserted into the inside of the insertion passage 35 of the opening portion 32, and thus, when the wire bending portion 71 is pulled to the proximal end side, the opening portion 32 is narrowed, and the bag part 3 is closed like a pouch. In addition, a length of the bending portion protruding from one pair of the first holes 23 to the outside can be adjusted by operating the first slider 61. For example, when the first slider 61 moves to the distal end side with respect to the operation part main body 63, the first wire 7 is moved to the distal end side with respect to the inner sheath 2, and the wire bending portion 71 is moved to the distal end side, whereby the opening portion 32 can be broadened from the closed state.

Figure 4:
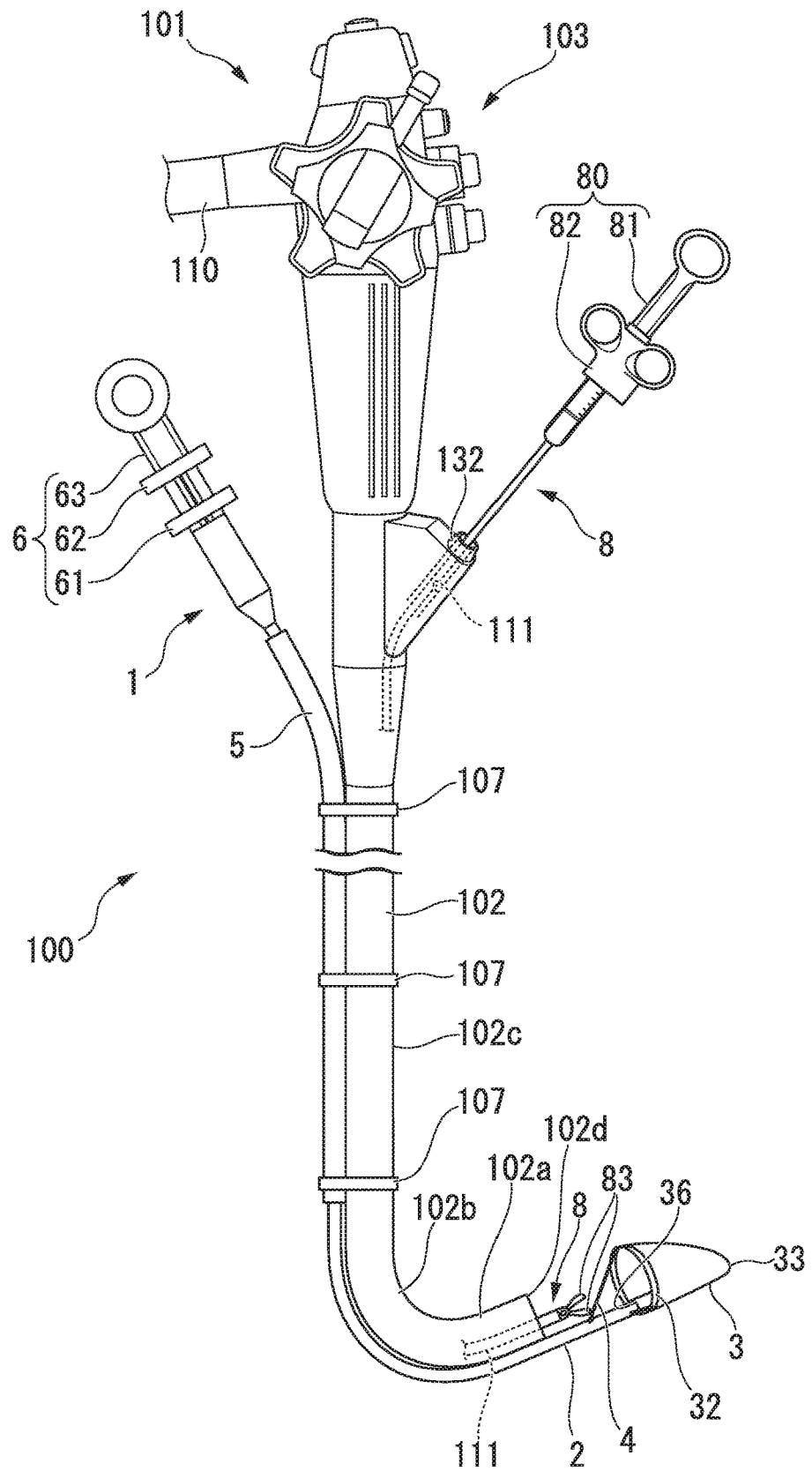
FIG. 4 is a diagram showing an endoscope system using a tissue collecting tool according to one embodiment of the present invention.

Next, a tissue collecting system 100 using the collecting tool 1 will be described. FIG. 4 is a diagram showing the tissue collecting system 100. As shown in FIG. 4, the tissue collecting system 100 according to this embodiment includes the collecting tool 1, an endoscope 101, an outer sheath 5, and grasping forceps 8.

The configuration of the endoscope 101 is not particularly limited. For example, in this embodiment, the endoscope 101 includes a flexible insertion part 102 and an operation part 103 of the endoscope 101 attached to the proximal end portion of the insertion part 102.

The insertion part 102 has flexibility and is formed in a columnar shape. Inside the insertion part 102, a plurality of channels 111 extending in the longitudinal direction are formed. A proximal end portion of the channel 111 is connected to a forceps port 132.

An observation unit, a light guide, and the like not shown in the drawing are provide in the plurality of channels 111. The observation unit includes an imaging device such as a CMOS image sensor or the like. The endoscope 101 further includes a display unit not shown in the drawing. The display unit is connected to the operation part 103 of the endoscope 101 through a universal cable 110. An image that is an observation target inside a predetermined viewing field acquired by the imaging device is converted into a signal, and the signal is transmitted to the display unit.

The insertion part 102 is provided by arranging a distal end rigid portion 102a, a bending portion 102b, and a flexible tube portion 102c from the distal end side in that order. In the distal end rigid portion 102a, an optical imaging mechanism (not shown in the drawing) used for optical observation is included. The bending portion 102b is configured to be bent in a predetermined direction by pulling an angle wire not shown in the drawing using the operation part 103 of the endoscope 101 for. The flexible tube portion 102c is a cylinder-shaped member that is flexibly formed to guide the distal end rigid portion 102a inside a luminal tissue or a body cavity to a desired position.

Figure 5:
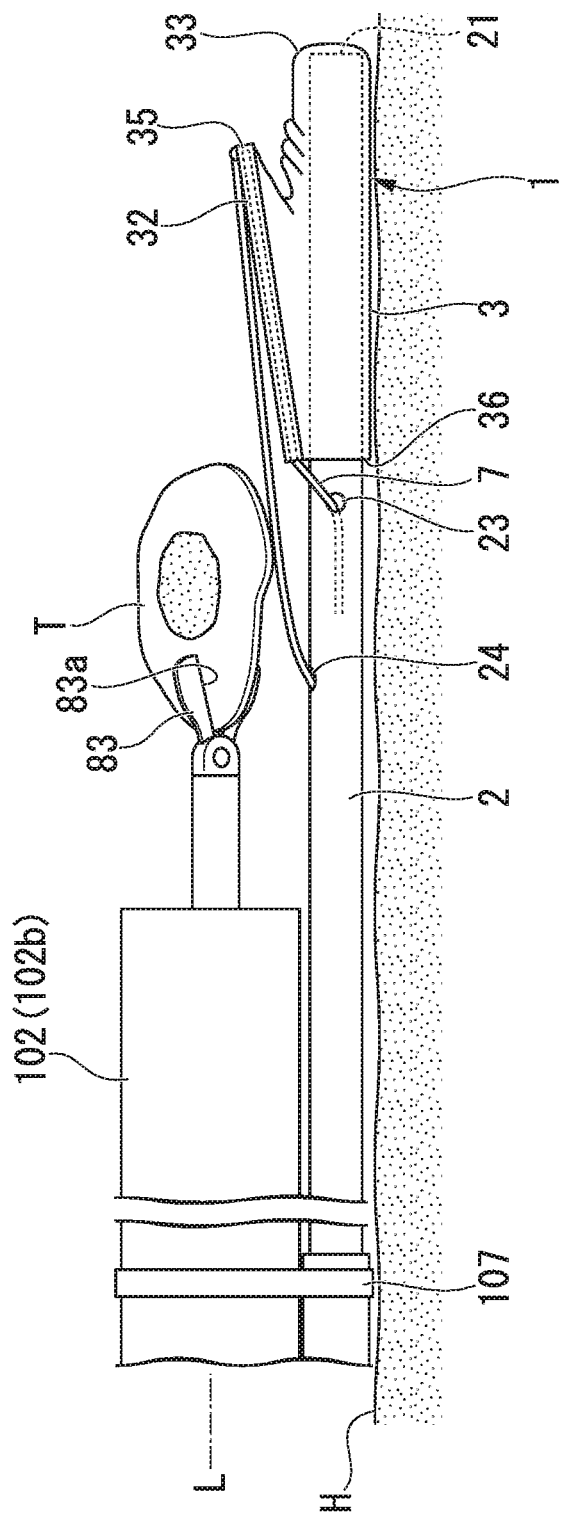
FIG. 5 is a diagram showing the usage form of a tissue collecting system according to one embodiment of the present invention.

The grasping forceps 8 is a known grasping forceps and is arranged to be inserted from the forceps port 132 of the endoscope 101 to the inside of the channel 111 of the insertion part 102 to be capable of protruding or retracting from the distal end of the insertion part 102. By moving a slider 82 of a forceps operating part 80 in the direction of the longitudinal axis L with respect to a forceps operating part main body 81, one pair of forceps 83 is operated to be open or closed. As shown in FIG. 5, in the one pair of forceps 83, grasping portions 83a having a concave-convex shape are formed at portions facing each other, and the one pair of forceps 83 is configured to stably grip a tissue when closed.

The outer sheath 5 is a flexible sheath arranged along the direction of the longitudinal axis L in an outer edge of the insertion part of the endoscope 101, and the inner sheath 2 is inserted into the outer sheath 5. The outer sheath 5 is arranged along the longitudinal axis in an outer edge portion of the insertion part 102 of the endoscope 101 and is fixed to the insertion part 102 by a fixing member.

The collecting tool 1 is arranged along the outer periphery of the insertion part 102 in parallel thereto and is attached to the insertion part using a plurality of fixing members 107 having ring shapes. The distal end of the outer sheath 5 is fixed to a further outer edge of the insertion part 102 closer to the proximal end of the insertion part 102 than the bending portion 102b of the insertion part 102. In this way, even in a case in which the direction of the opening portion 32 of the collecting tool 1 does not face that of the grasping forceps 8, by moving the bending portion 102b of the insertion part 102 by operating the operation part 103 of the endoscope 101, the grasping forceps 8 and the opening portion 32 of the collecting tool 1 can be positioned to face each other. The outer sheath 5 is a flexible sheath, and thus is bent to follow a bending operation of the insertion part 102.

As shown in FIG. 1, the bag part 3 is arranged in a state in which it protrudes further to the distal end side than the inner sheath 2. The collecting tool 1 is inserted into the inside of the body in this state.

Figure 6:
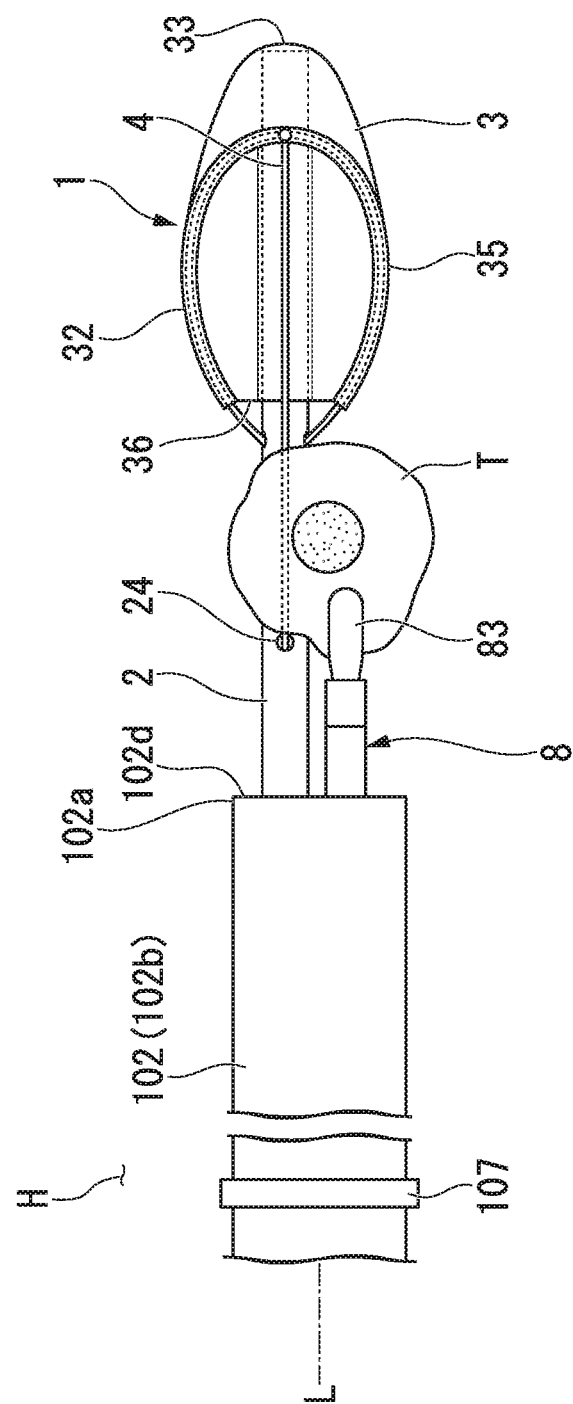
FIG. 6 is a diagram showing the usage form of a tissue collecting system according to one embodiment of the present invention.

Next, a procedure using the tissue collecting system 100 will be described with reference to FIGS. 5 to 10. In this procedure, a procedure of collecting a tissue acquired by ablating a treatment target portion inside a luminal organ H by using an ablation treatment tool such as a high-frequency incision tool that is not shown in the drawing is performed. First, an operator performs oral insertion of the insertion part 102 of the endoscope 101 in which the collecting tool 1 is attached to the inside of a body. Next, as shown in FIGS. 5 and 6, by pushing the operation part 6 to cause the inner sheath 2 to protrude from the distal end of the outer sheath 5, the collecting tool 1 is caused to protrude further to the distal end side than the distal end rigid portion 102a of the insertion part 102.

The operator grasps a resected tissue T of a lesion part that is resected by the high-frequency incision tool by using the grasping forceps. Next, the operator causes one pair of the forceps 83 grasping the resected tissue T to retreat to a position near a distal end surface 102d of the insertion part 102 and operates the operation part 103 of the endoscope 101 to return the bending portion 102b of the insertion part 102 to be in the direction of the longitudinal axis L. At this time, as shown in FIG. 6, the one pair of the forceps 83 and the resected tissue T are arranged on a further proximal end side than the bag part 3.

Figure 7:
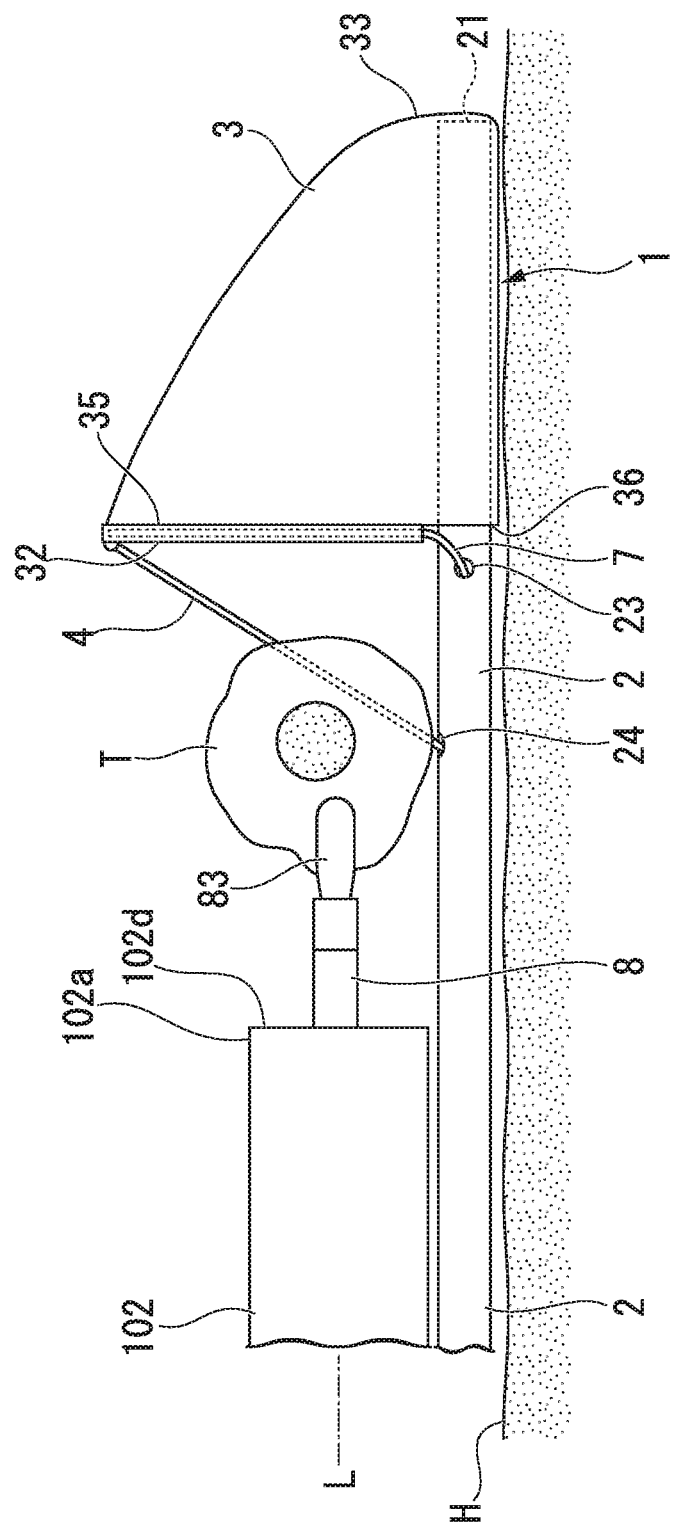
FIG. 7 is a diagram showing the usage form of a tissue collecting system according to one embodiment of the present invention.

Subsequently, the operator performs an operation of pulling the second slider 62 of the operation part 6 of the collecting tool 1 to the proximal end side and moves the string 4 to the proximal end side, thereby causing the opening portion 32 to be raised to cause the bag part 3 to be in the open state. As shown in FIG. 7, the opening portion 32 is raised by changing the direction of the opening and is open at a position facing the distal end surface 102d of the insertion part 102, and the one pair of the forceps 83 and the resected tissue T are positioned between the opening portion 32 and the distal end surface 102d of the insertion part 102. At this time, there are cases in which the direction of the raised opening portion 32 does not face the grasping forceps 83. In such cases, by moving the bending portion by operating the operation part 103 of the endoscope 101, the grasping forceps 83 and the opening portion 32 are adjusted to face each other.

Figure 8:
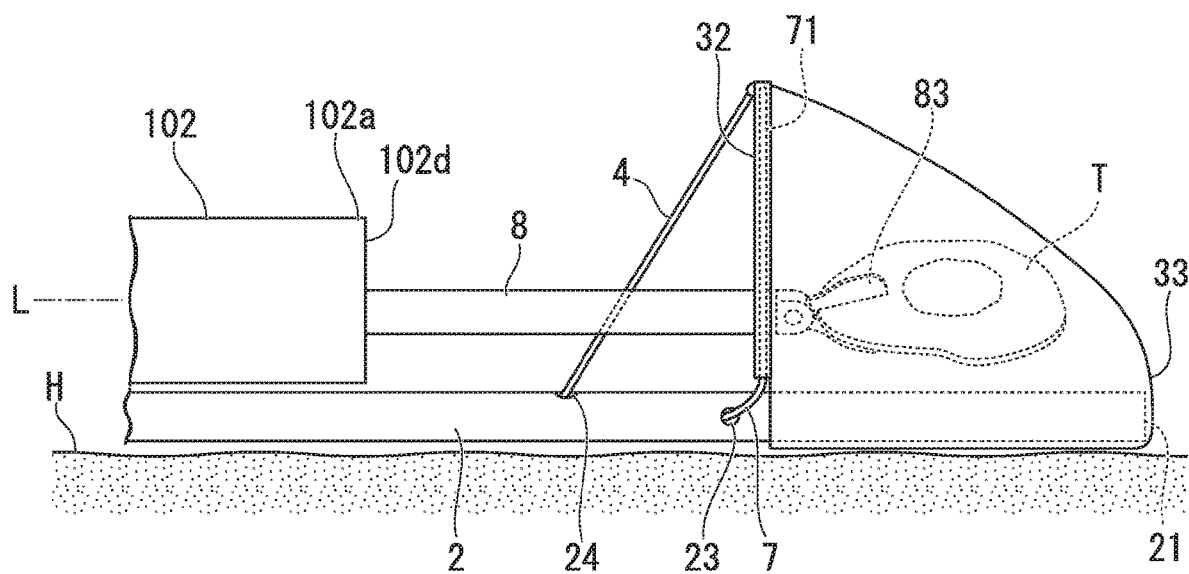
FIG. 8 is a diagram showing the usage form of a tissue collecting system according to one embodiment of the present invention.

Next, as shown in FIG. 8, the operator pushes the operating part 80 of the grasping forceps 8 to the distal end side and advances the one pair of the forceps 83 grasping the resected tissue T that is in the state of grasping the resected tissue T to be accommodated inside the bag part 3.

At this time, also after the bending portion 71 of the first wire 7 is raised in a direction that is approximately orthogonal to the longitudinal axis L of the inner sheath 2, in a case in which the second slider 62 is further operated to be pulled to the proximal end side, the bending portion 71 of the first wire 7 is elastically transformed. As a result, as shown in FIG. 6, in the closed state, an opening having an oval shape that is long in the direction of the longitudinal axis L can be changed to a shape closer to a circular shape. The operator can adjust the opening width of the opening portion 32 by adjusting the amount of the operation of the second slider 62 in accordance with the size of a resected tissue T grasped by the one pair of the forceps 83, and accordingly, the resected tissue T can be inserted into the inside of the bag part 3 more smoothly. In addition, when a resected tissue T is inserted into the inside of the bag part 3, the direction of the one pair of the forceps 83 may be adjusted in accordance with the shape or the size of the resected tissues T, and then, the resected tissue T may be inserted.

Figure 9:
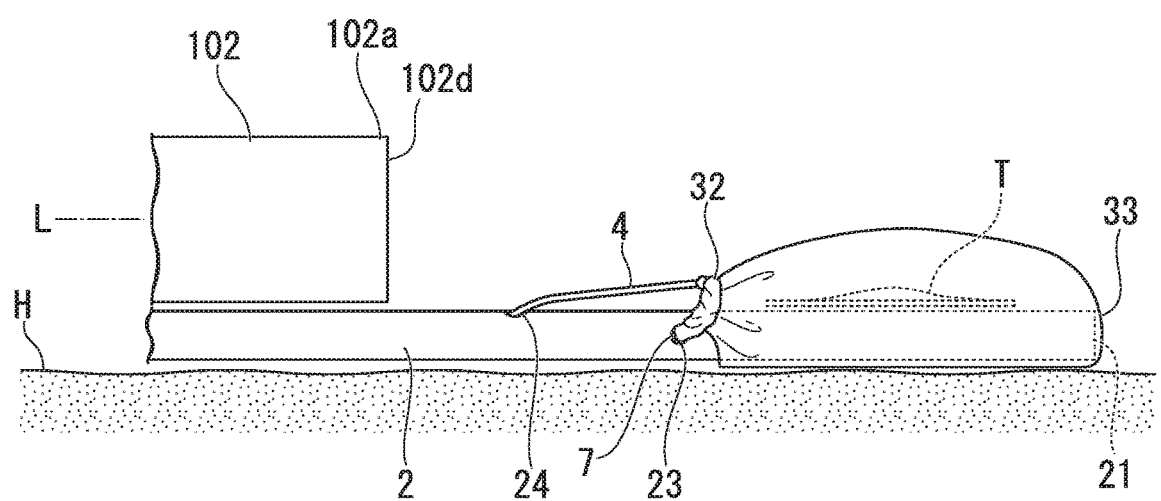
FIG. 9 is a diagram showing the usage form of a tissue collecting system according to one embodiment of the present invention.
Figure 10:
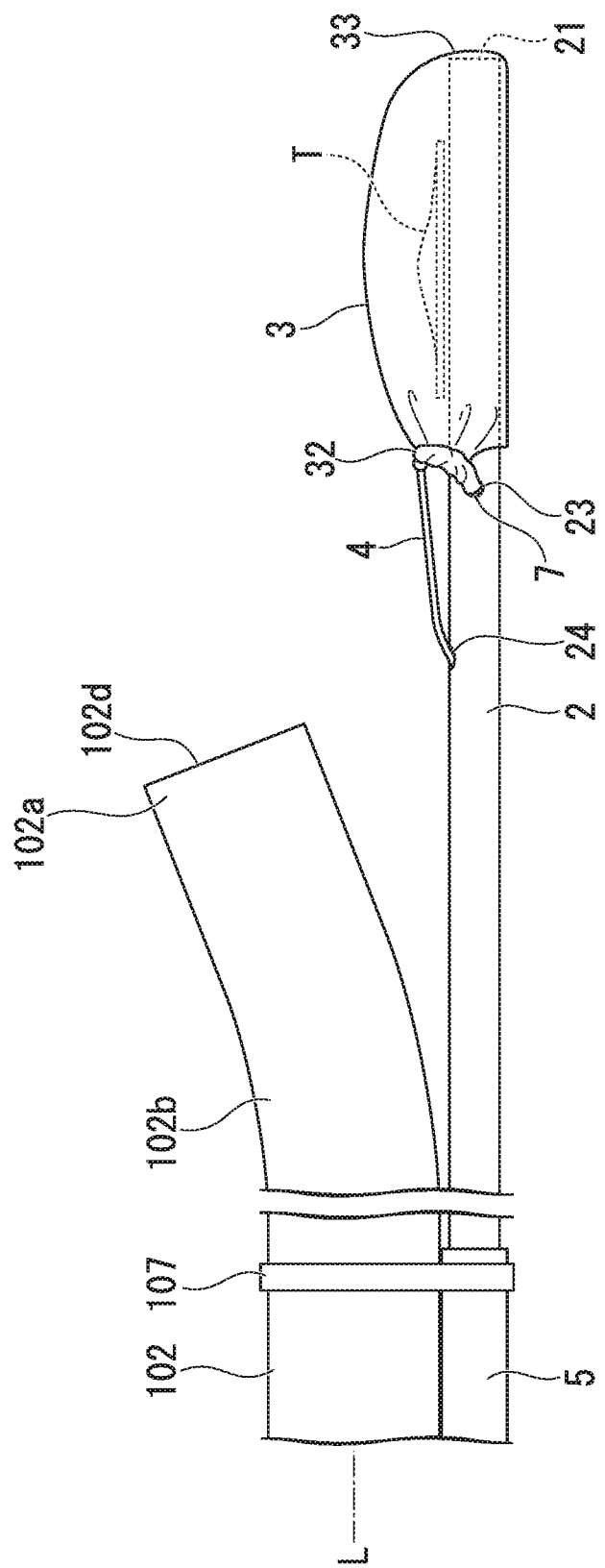
FIG. 10 is a diagram showing the usage form of a tissue collecting system according to one embodiment of the present invention.

In a case in which the resected tissue can be inserted into the inside of the bag part 3, the operator opens the one pair of the forceps 83 and separates the resected tissue T to be accommodated inside the bag part 3. Next, the operator causes the one pair of the forceps 83 to retreat to the proximal end side to be accommodated inside the channel 111 of the insertion part 102. Subsequently, as shown in FIG. 9, the operator pulls the first slider 61 of the collecting tool 1 to the proximal end side to decrease the amount of protrusion of the bending portion 71 of the first wire 7 that protrudes from the inner sheath 2 toward the outside and closes the opening portion 32. Thereafter, as shown in FIG. 10, the operator observes the periphery of the resected portion by bending the bending portion 102b of the insertion part 102 as is necessary.

Next, the inner sheath 2 is pulled to the proximal end side with respect to the outer sheath 5, and the endoscope 101 is removed from the inside of the body in this state. The resected tissue T is collected to the outside of the body while the resected tissue T is protected by being accommodated inside the bag part 3, and the procedure of collecting the resected tissue T ends.

As described above, according to the collecting tool 1 and the tissue collecting system 100 of this embodiment, by attaching the collecting tool 1 to an existing endoscope apparatus, a resected tissue T can be easily accommodated in the bag part 3, and the collecting of the resected tissue T outside the body can be appropriately performed.

In the collecting tool 1, because the opening portion 32 can be raised such that the opening portion 32 faces the distal end surface of the insertion part by pulling the string 4, the resected tissue T can be easily moved to the inside of the bag part 3 by only performing an advancement and a retreatment operation of the one pair of forceps 83 grasping a tissue with respect to the endoscope 101. In addition, the operation at this time can be easily checked using the imaging mechanism arranged in the distal end rigid portion 102a of the insertion part 102.

In the collecting tool 1, a resected tissue T is collected to the outside of the body in the state being accommodated inside the bag part 3, and accordingly, the resected tissue T can be easily removed to the outside of the body without being left. In addition, in a collecting route in which the insertion part 102 is removed, the resected tissue T is prevented from being in contact with a tissue of a luminal organ H or the like, and the resected tissue T can be securely removed to the outside of the body. Particularly, in a case in which the opening portion 32 is in the closed state by causing the first wire 7 to retreat, the resected tissue T accommodated inside the bag part 3 can be separated more reliably, and accordingly, drop-out of the resected tissue H or a contact with a luminal organ H that is present in the collecting route can be more reliably prevented.

In the collecting tool 1, by inserting the string 4 into the inside of the lumen 22 of the inner sheath 2, the advancement and the retreatment operation of the inner sheath 2 with respect to the outer sheath 5 can be smoothly performed.

The configuration of the collecting tool 1 according to this embodiment may be variously changed as described below.

In this embodiment, while an example in which one string 4 is arranged is shown, a plurality of strings 4 may be arranged and connected to a plurality of positions in the peripheral direction of the opening portion 32. By disposing a plurality of strings 4, the opening portion 32 can be maintained in a more circular shape, and a resected tissue T can be easily inserted into the inside of the bag part 3.

Since the outer sheath 5 is fixed to a further proximal end side than the bending portion of the insertion part, a bending operation of the bending portion is not disturbed by the collecting tool at the time of performing a treatment using the grasping forceps or the like, and the bending operation of the insertion part can be smoothly performed.

In this embodiment, while an example in which the main body is the inner sheath has been described, a configuration in which the opening portion is raised by moving a linear member in the longitudinal axis direction with respect to the main body may be employed, and, for example, the main body may be a shaft member. In such a case, for example, a configuration may be employed in which a ring-shaped member instead of the first wire is used, the ring-shaped member is inserted into a through hole or a hole, which is formed in a direction orthogonal to a longitudinal axis of the main body, to be rotatable, and a linear member is arranged along the main body for raising the bag part 3.

In this embodiment, while an example in which the string 4 is inserted into and passes through the lumen 22 of the inner sheath 2 has been described, the string 4 may be configured to advance or retreat with respect to the inner sheath 2 on the operation part 6 side, and, for example, the sting 4 may be configured to be inserted between the inner sheath 2 and the outer sheath 5 and operated on the proximal end side of the outer sheath 5.

In this embodiment, although the bag part 3 has been described as a bag formed by a thin film that is formed using vinyl as an example, in a case in which a resected tissue that is not required to be separated is collected, for example, a net having a bag shape may be used. Here, in a case in which there is concern of seeding according to the resected tissue as in the case of a procedure of ablating a malignant tumor, by using a bag formed by an impermeable film, the resected tissue can be delivered to the outside of the body in a separated state.

Figure 11:
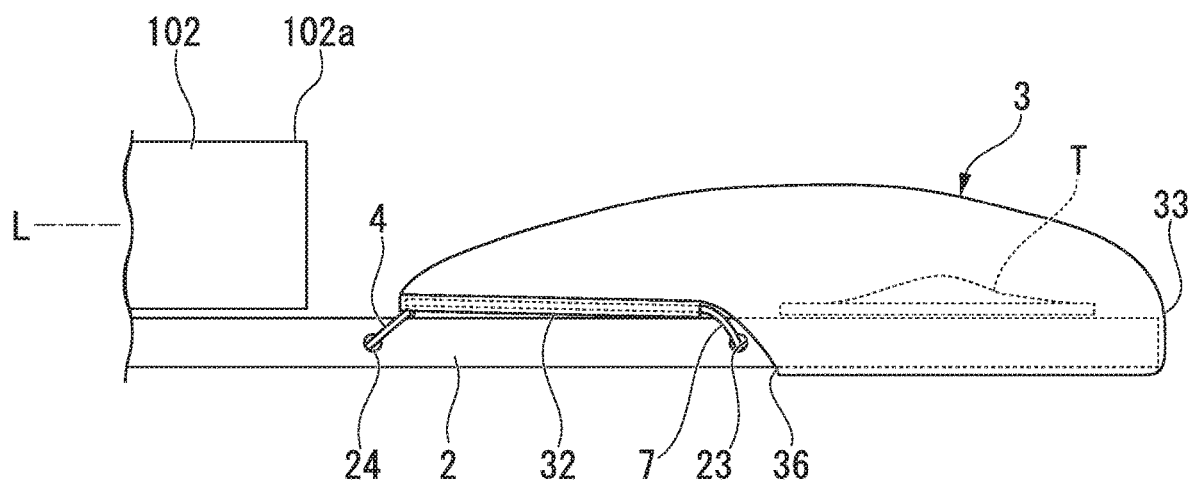
FIG. 11 is a diagram showing a modified example of a tissue collecting system according to one embodiment of the present invention.

In this embodiment, while an example in which a configuration for contracting the opening portion 32 by pulling the first wire 7 to the proximal end side is included has been described, such a configuration is not essential. For example, as shown in FIG. 11, a configuration may be employed in which, by pulling a string to the proximal end side, the bending portion protruding from the inner sheath to the outside is rotated to the proximal end side by using one pair of first holes 23 as starting points, and the opening portion 32 is brought into contact with the inner sheath.

In this embodiment, while a configuration in which the inner sheath 2 of the collecting tool 1 is inserted into and passes through the outer sheath 5 has been described as an example, such a configuration is not essential. For example, by causing the inner sheath 2 to be inserted into and pass through the outer sheath 5, the collecting tool 1 can be smoothly moved in the direction of the longitudinal axis L, in a case in which the collecting tool 1 is attached in a state in which the position in the direction of the longitudinal axis L with respective to the insertion part 102 of the endoscope 101 is determined, the outer sheath 5 is unnecessary.

As above, while each embodiment of the present invention has been described, the technical scope of the present invention is not limited to the embodiments described above, and, in a range not departing from the concept of the present invention, a combination of constituent elements in each embodiment may be changed, or various changes or deletions may be made in each of the constituent elements. The present invention is not limited to the description presented above.

What is claimed is:

1. A tissue collecting tool comprising:
a main body having an elongate shape extending along a longitudinal axis from a proximal end to a distal end;
an operation part comprising a slider, the operation part being provided in a proximal end side of the main body;
a bag which includes a bottom and an opening, the opening including a fixed part that is fixed to the main body such that the opening is positioned proximal of the bottom;
a string which is connected to the opening and the operation part and which is configured to move with respect to the main body in a proximal direction along the longitudinal axis of the main body so as to raise the opening with respect to the main body; and
a wire which is provided along the opening and which is capable of being elastically transformed,
wherein:
in the bag, the string and the wire are connected to the opening at positions separate from the fixed part of the opening, and
a distal portion of the wire, starting at a position adjacent to the fixed part of the opening, is configured to be raised with respect to the main body when the string is moved with respect to the main body in the proximal direction along the longitudinal axis.

2. The tissue collecting tool according to claim 1, wherein:
the main body is a tube-shaped member, and
the string is inserted into a lumen of the main body from a hole formed at a position proximal of the fixed part of the opening of the bag, and a proximal end portion of the string is connected to the operation part.

3. The tissue collecting tool according to claim 2, wherein:
the wire includes:
a bending portion that is inserted into the lumen of the main body and is exposed outside the main body through a through hole formed on a side face of the main body, and is arranged in the opening; and
a proximal end portion that is connected to the operation part at the proximal end side of the main body, and
an opening width of the opening is configured to be adjustable by a movement of the wire with respect to the main body in the direction along the longitudinal axis.

4. The tissue collecting tool according to claim 1, wherein the bag is configured to be moved between: (i) a delivery configuration in which the bag is collapsed and the opening of the bag is disposed along the main body in an open state so as to face away from the main body, and (ii) a tissue-receiving configuration in which the bag is expanded, and the opening of the bag is in an open state and is raised with respect to the main body so as to face in a proximal direction along the longitudinal axis of the main body.

5. The tissue collecting tool according to claim 1, wherein the bag is configured to be moved between: (i) a delivery configuration in which the bag is collapsed and the opening of the bag is disposed along the main body in an open state so as to face away from the main body, (ii) a tissue-receiving configuration in which the bag is expanded, and the opening of the bag is in an open state and is raised with respect to the main body so as to face in a proximal direction along the longitudinal axis of the main body, and (iii) a retrieval configuration in which the opening of the bag is closed against the main body.

6. The tissue collecting tool according to claim 1, wherein the wire is configured to bend at a position adjacent to the fixed part of the opening of the bag when the string is moved with respect to the main body in the proximal direction along the longitudinal axis of the main body.

7. The tissue collecting tool according to claim 1, wherein, when the string is moved in the proximal direction, the wire is configured such that the bag is moved from a collapsed state, in which the opening of the bag faces away from the main body, to an open state, in which the opening of the bag is raised so as to be oriented in a substantially vertical direction relative to the longitudinal axis of the main body.

8. A tissue collecting system comprising:
an endoscope which includes a flexible insertion part;
the tissue collecting tool according to claim 1 that is arranged in a direction of a longitudinal axis of the flexible insertion part on an outer edge of the flexible insertion part; and
grasping forceps which are inserted into a channel formed in the flexible insertion part.

9. The tissue collecting system according to claim 8, wherein
the bag is configured to be opened such that the opening is raised so as to face a distal end of the flexible insertion part by moving the string in the proximal direction along the longitudinal axis of the main body with respect to the main body in a state in which the bag is pushed forward from a distal end of the flexible insertion part of the endoscope.

10. The tissue collecting system according to claim 8, wherein
the tissue collecting tool is fixed on the outer edge of the flexible insertion part at a position proximal of a bending portion of the flexible insertion part.

11. A method of collecting tissue using the tissue collecting tool according to claim 1 in a state where the tissue collecting tool is attached in an insertion part of an endoscope, the method comprising:
inserting the insertion part into a body;
advancing the tissue collecting tool in a distal direction such that the tissue collecting tool protrudes distally from a distal end of the insertion part; raising the opening by moving the string in a proximal direction along the longitudinal axis of the main body of the tissue collecting tool, and causing the bag to be in an open state;
collecting the tissue inside the bag; and
retracting the bag to an outside of the body while the tissue is accommodated inside the bag.

12. The method of collecting the tissue according to claim 11, further comprising closing the opening after the tissue is collected inside the bag by decreasing an amount of protrusion of the wire from the main body.

* * * * *